United States Patent [19]

Agarwal et al.

[11] Patent Number: 4,751,224
[45] Date of Patent: Jun. 14, 1988

[54] TREATMENT OF METASTASIS

[75] Inventors: Kailash C. Agarwal, Lincoln; Robert E. Parks, Jr., Providence, both of R.I.

[73] Assignee: Brown University Research Foundation, Providence, R.I.

[21] Appl. No.: 820,923

[22] Filed: Jan. 21, 1986

Related U.S. Application Data

[63] Continuation-in-part of Ser. No. 516,182, Dec. 14, 1983.

[51] Int. Cl.$^4$ .................. A61K 31/50; A61K 31/70; A61K 31/51; A61K 31/505; A61K 31/52; A61K 31/47; A61K 31/45; A61K 31/19
[52] U.S. Cl. ........................... 514/248; 514/46; 514/218; 514/258; 514/264; 514/307; 514/455; 514/573
[58] Field of Search ............... 514/455, 307, 218, 258, 514/264, 46, 573, 248

[56] References Cited

U.S. PATENT DOCUMENTS 4,088,659 5/1978 Bhat et al. .
4,118,508 10/1978 Bhat et al. .
4,134,986 1/1979 Bajwa et al. .
4,476,140 10/1984 Sears et al. ................... 424/283

FOREIGN PATENT DOCUMENTS 0116713 8/1984 European Pat. Off. ............ 514/248

OTHER PUBLICATIONS

Hoover et al., "Techniques for Inhibiting Tumor Metastases", Cancer, vol. 35, Jan. 1975, p. 512.
Gasic et al., "Anti-Metastatic Effect of Aspirin", The Lancet, Oct. 28, 1972.
Honn et al., "Prostacyclin and Thromboxanes Implications for Their Role in Tumor Cell Metastasis", Biochemical Pharmacology, Vo. 32, No. 1, pp. 1–11, 1983.
Bhat et al., "Structures and Stereochemistry of New Labdane Diterpenoids from Coleus Forskohlii Briq.$^1$", Tetrahedron Letters, No. 19, pp. 1669–1672, 1977.
Adnot et al., "Forskolin (A Powerful Inhibit or of Human Platelet Aggregation)", Biochemical Pharmacology, vol. 31, No. 24, pp. 4074–4076, 1982.
Bhat et al., "The Antihypertensive and Positive Inotropic Diterpene Forskolin: Effects of Structural Modifications on its Activity", J. Med. Chem. 26, pp. 486–492, 1983.
de Souza et al., "Forskolin: A Labdane Diterpenoid With Antihypertensive, Positive Inotropic . . . ", Medicinal Research Reviews, vol. 3, No. 2, pp. 201–219 1983.
Agarwal & Parks, "Synergistic Inhibition of Platelet Aggregation by Forskoliln Plus . . . ", Biochemical Pharmacology, vol. 31, No. 22, pp. 3713–3716, 1982.
"Structure-Activity Relationships for Activation of Adenylate Cyclase by the Diterpene Forskolin and its Derivatives", Seamon et al., J. Med. Chem., 1983, 26, pp. 436–439.

*Primary Examiner*—Jerome D. Goldberg
*Attorney, Agent, or Firm*—Thomas J. Engellenner

[57] ABSTRACT

A method for reducing the incidence of metastasis in tumor victims without treating the primary tumor per se resides in the administration of forskolin or its analogs which are potent inhibitors of platelet aggregation. Forskolin compounds are generally defined as labdane diterpenoids having the general formula:

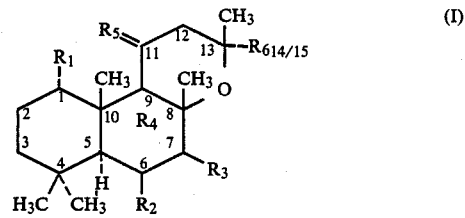

These compounds may be administered alone or in combination with other inhibitors of platelet aggregation.

10 Claims, 1 Drawing Sheet

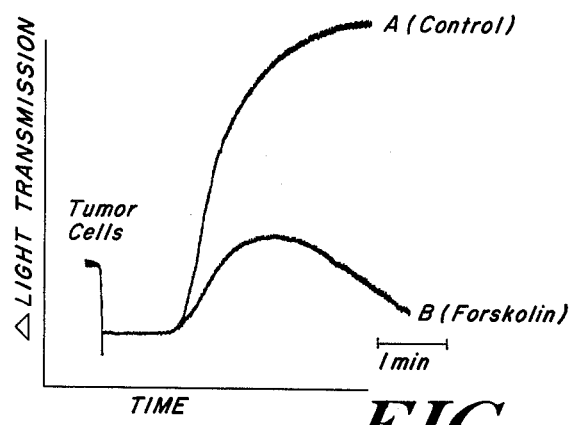
FIG. 1
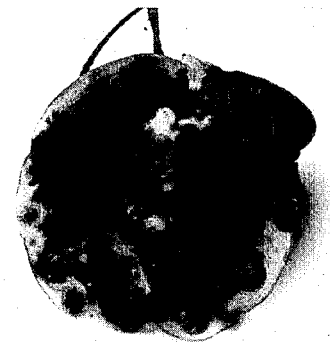 
UNTREATED CONTROLS
FIG. 2A
FORSKOLIN TREATED
FIG. 2B
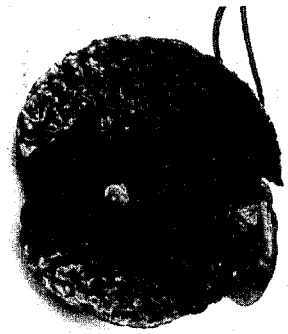 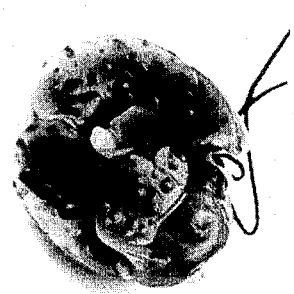
FIG. 2C
FIG. 2D

TREATMENT OF METASTASIS

TECHNICAL FIELD

This invention concerns methods and compositions for the treatment of tumor-induced metastasis, in particular, hematogeneous metastasis. The U.S. Government has rights in this invention pursuant to grants Nos. CA 13943 and CA 07340 provided by the U.S. Public Health Service.

This application is a continuation-in-part of application Ser. No. 516,182, filed Dec. 14, 1983.

BACKGROUND OF THE INVENTION

Advances in surgical and radiation treatment of primary tumors have left metastasis as perhaps the most devastating aspect of cancer. In operable cases, primary tumor growth or local recurrence is rarely a cause of death. Instead, at present, roughly one-third of cancer victims with operable tumors ultimately succumb to metastatic disease.

The hematogeneous metastatic process begins with the detachment of tumor cells from the primary tumor followed by intravasation with direct shedding of tumor cells into circulation. Although most tumor cells in circulation are quickly destroyed by various mechanisms, a few viable cells may be arrested in the microvasculature or otherwise may adher to endothelial surfaces.

While in the blood stream or shortly after adhesion to endothelium, intravascular cancer cells become surrounded by thrombotic material consisting of platelets, erythrocytes and fibrin. Thrombus formation appears to be a significant event in the establishment of tumor colonies in the capillary beds of various organs. Blood platelets also appear to play an important role in tumor metastasis; it has been demonstrated that many metastasizing tumor cell lines induce platelet aggregation both in vitro and in vivo. Furthermore, upon aggregation, platelets release a substance or substances which promote tumor growth.

Since tumor cell-platelet interactions play a role in tumor metastasis, several laboratories have examined anticoagulants and anti-aggregating agents, such as heparin, warfarin (Hagmar and Norrby, Vol. 5 *Int. J. Cancer*, pp. 72-84, [1970]; Lione and Bosmann, Vol. 2 *Cell Biol. Int. Res.*, pp. 81-86 [1972]; Hoover and Ketcham, Vol. 35 *Cancer*, pp. 5-14 [1975]); aspirin (Gasic et al., *Lancet II*, pp. 932-933 [1972]; Wood and Hilgard, *Lancet II*, pp. 1416-1416 [1972]; Hilgard et al., Vol. 86 *Z. Krebsforsch.*, pp. 243-250 [1976]) and dipyridamole (Hilgard in *Interaction of Platelets and Tumor Cells*, pp. 143-158, Jameson [ed.] [1982]; Ambrus et al. in *Platelets: A Multidisciplinary Approach*, pp. 467-48, de Gaetano [ed.] [1982]) to reduce the incidence of tumor metastasis without treating the tumor per se in experimental animal models. However, the results of many of these studies were inconclusive. Recent reports by Honn et al., 212 *Science*, pp. 1270-1272 (1981) have shown that i.v. injection of prostacyclin (PGI$_2$), a potent inhibitor of platelet aggregation, reduces pulmonary tumor colonization by tail vein injected B16 amelanotic melanoma cells in mice.

There exists a need for new and effective agents for treatment and prevention of metastasis which do not treat the primary tumor per se but which can be used in conjunction with surgery and/or tumor chemotherapy. In particular, agents that are capable of reducing the incidence of metastasis by inhibiting platelet aggregation without harmful side-effects would satisfy a long-felt medical need.

SUMMARY OF THE INVENTION

It has been discovered that a method for reducing the incidence of metastasis in tumor victims without treating the primary tumor per se resides in the administration of forskolin or its analogs which are potent inhibitors of platelet aggregation. Forskolin compounds are generally defined as labdane diterpenoids having the general formula:

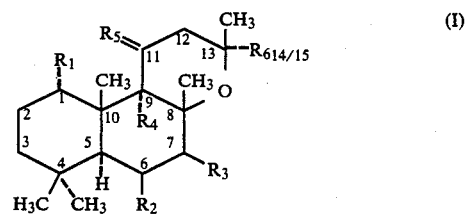

where $R_1$ is hydrogen or a hydroxy or lower alkoxy, sulfonate or carbonate group;

where $R_2$ is a hydroxy, carbonate, acetyl, or acetoxy or lower alkanoyl group;

where $R_3$ is a hydroxy, carbonate, acetyl or acetoxy or lower alkanoyl or tosyl group;

where $R_4$ is a hydrogen or a hydroxy or lower alkoxy, sulfonate or carbonate group;

where $R_5$ is either double-bonded oxygen or separately bound hydrogen and hydroxy groups; and where $R_6$ is a lower alkene or oxygen. (The term "lower" is used herein to describe substituents having alkyl chains containing 1 to 6 carbon atoms.)

In particular, we have found that 7 beta-acetoxy-8,13-epoxy-1 alpha,6 beta,9 alpha trihydroxy-labd-14-en-11-one (forskolin) is effective in preventing the metastasis of mouse melanoma tumor cells. This compound is defined by the following formula:

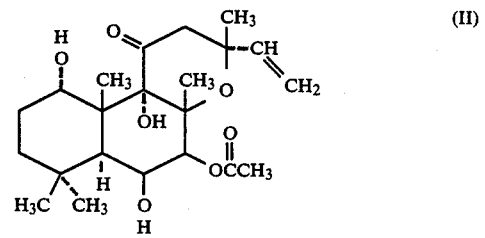

It appears that the forskolin blocks human platelet aggregation (induced by a wide variety of aggregation stimulators) by stimulating membrane adenylate cyclase thereby increasing several-fold the intracellular concentrations of cyclic AMP and inhibiting the tumor cell-platelet interactions, which seem to play a role in tumor metastasis, without effecting the tumor cells per se.

We have demonstrated that forskolin strongly inhibits the melanoma cell-induced human platelet aggregation in vitro. Additionally, we have shown that forskolin, administered intraperitoneally to live animals prior to tail vein injections of cultured cancer cells, reduced tumor colonization in the lungs by more than 70 percent without effecting the melanoma cells directly. Moreover, the inhibitory effects of forskolin in vitro have been shown to be potentiated by the combination of this agent with other anti-aggregating compounds, such as prostaglandin E, and 2-fluoroadenosine (F-Ado).

Our experiments also indicate that forskolin compares favorably with $PGI_2$ when in vivo activity in reducing metastasis is measured. Although $PGI_2$, compared to forskolin on a molar basis, is several hundred-fold more potent in inhibiting the platelet aggregation in vitro, the potencies of $PGI_2$ and forskolin as inhibitors of pulmonary tumor metastasis are similar. According to Honn, doses of $PGI_2$ in the range of 50–200 micrograms/mouse were required to obtain decreases in pulmonary tumor foci of greater than 50 percent. Our studies show that a single dose of forskolin (82 microgram/mouse, i.p.) reduced pulmonary colonization by more than 70 percent. Forskolin may be unique in its action and perhaps interacts directly with the catalytic subunit of adenylate cyclase. Thus, forskolin's high activity coupled with its low toxicity (reported LD 50 values for mice are 105 mg/kg i.p. and 3,100 mg/kg per OS) suggest that it can be a highly effective agent in reducing metastasis while not treating the primary tumor per se.

The invention will next be described in connection with certain preferred embodiments; however, it should be clear that various changes and modifications can be made by those skilled in the art without departing from the spirit and scope of the invention. For example, although the experiments reported herein employed the 7 beta-acetoxy-8,13-epoxy-1 alpha,6 beta,9 alpha-trihydroxy-labd-14-en-11-one compound forskolin, various analog compounds can be expected to exhibit similar properties. See generally, Bhat et al., "Structures and Stereochemistry of New Labdone Diterpenoids from Coleus Forskohlii Briq.", *Tetrahedron Letters*, pp. 1669–1672 (1977); Adnot et al., "Forskolin (a powerful inhibitor of human platelet aggregation)", Vol. 31, *Biochemical Pharmacology*, pp. 4071–4074 (1982); Bhat et al., "Antihypertensive and Positive Inotropic Diterpane Forskolin: Effects of Structural Modifications on its Activity", Vol. 26, *J. Med. Chem.*, pp. 486–492 (1983) and DeSouza et al., "Forskolin: A Labdane Diterpenoid with Antihypertensive, Positive Inotropic, Platelet Aggregation Inhibitory, and Adenylate Cyclase Activating Properties", Vol. 3, *Medicinal Research Reviews*, pp. 201–219 (1983), all of which are incorporated herein by reference, for discussions of pharmalogically active forskolin analogs.

Specifically, forskolin analogs with similar properties include various modifications of the groups labeled $R_1$ to $R_6$ in formula I above. The 6-hydroxy group may be acetylated. The 7-acetyl group may be removed or replaced by n-alkaroyl or tosyl groups. The delta 14,15 bond may be substituted by oxygen. 1,9-dideoxyforskolin as well as the 6,7-carbonate and the 1,9:6,7-dicarbonate may also be effective. The 6-acetyl-7-deacetyl derivative also appears to be active as do compounds where the chain length of the 6-alkanoyl group is increased or diethyl-aminocthyl groups are introduced at the 1-position. Moreover, 7-Deacetyl-11-deoxo-11 beta-hydroxyforskolin and 1-methyl-6 acetyl-7 deacetyl derivatives also appear to be pharmacologically active.

Tumor victims, as the term is used herein, refers to humans and animals.

The forskolin compounds described above may be administered alone or in conjunction with other agents. The forskolin compounds may be combined with nucleoside transport inhibitors which retard the uptake of adenosine by red blood cells and the like; such inhibitors include p-nitrobenzylthioinosine and dilazep. Our compounds may also be combined with agents that block the action of cAMP phosphodiesterase in converting cAMP to AMP, such as theophylline analogs, or compounds that both inhibit nucleoside transport and block cAMP conversion, such as dipyridamole and its analogs (i.e., RA-233), oxagrelate and papaverine. Additionally, the forskolin compounds may be combined with other compounds that act upon adenylate cyclase in different fashions to create a synergistic effect; such compounds include adenosine analogs and prostacyclins.

BRIEF DESCRIPTION OF THE FIGURES

FIG. 1 is a graph plotting in vitro human platelet aggregation induced by the melanoma cells. (A) control (B) after treatment of platelet-rich plasma with forskolin.

FIGS. 2a–2d are photographs comparing representative lung specimens from forskolin-treated and untreated mice.

DESCRIPTION OF THE PREFERRED EMBODIMENTS

The following non-limiting working examples illustrate our invention.

EXAMPLE I

A mouse melanoma subline, B16–F10, (highly metastatic to the lungs) was obtained from EG & G Mason Research Institute, Worcester, MA, and adapted to growth in cell culture. The cultured cells were harvested by 1 min of trypsinization (0.25% trypsin-0.1% EDTA) or with the use of a rubber policeman, washed gently three times with Hank's balanced salts solution (HBBS, free of $Ca^{++}$ and $Mg^{++}$). The cell viability determined by Trypan Blue exclusion ranged from 70–95% in the separate experiments. Freshly drawn whole blood from healthy adult human donors was anticoagulated with heparin (5 units/ml). The donors had not ingested antiplatelet drugs for at least 10 days. Platelet-rich plasma (PRP) was separated by centrifugation of the whole blood and platelet aggregation was measured in PRP by recording the increase in light transmission after the addition of the tumor cells.

Washed B16–F10 cell suspensions ($2 \times 10^7$/ml) were treated with potato apyrase (1 unit/ml) for about 5 min to degrade exogenous adenine nucleotides. Fifty microliters of the cell suspension was then added to the platelet-rich plasma after an incubation of 5 min with (A) 5 microliters DMSO (10% in saline) (Control) or (B) 5 microliters forskolin (200 micro Molars in DMSO 10% in saline). Final concentration of forskolin in PRP (500 microliters) was 2 micromolars. FIG. 1 shows that B16–F10 cells ($2 \times 10^6$/ml) induced human blood platelet aggregation after a lag of about 1 min. However, if the PRP was preincubated (5 min) with the low concentration of forskolin (2 micromolars), the tumor cell-induced platelet aggregation was strongly blocked.

EXAMPLE II

Intravenous tail vein injections of B16–F10 cells (2 or $3 \times 10^5$ cell/mouse) to C57BL/6 mice (5–8 weeks old, 6–9 mice/group), produced a large number of pulmonary tumor foci after 9 or 14 days. However, if the mice were treated with a single intraperitoneally dose of forskolin (82 micrograms/mouse, i.e. 4–5 mg/kg) given 30 or 60 min before the tumor cell injections, reductions in tumor colonization of greater than 70 percent were observed without treating the injected tumor cells per se. Similar results were seen in three separate experiments.

Washed B16-F10 tumor cells (2 or $3 \times 10^5$) in 100 microliters Hanks balanced salts solution were injected from the tail vein 60 min (Exp. 1) or 30 min (Exp. 2, 3) after i.p. injection of 200 microliters DMSO (20 percent in saline) in control group; or forskolin (5 mM) prepared in DMSO (100 percent) and diluted to 1 mM with saline just before injection. The mice were sacrificed after 9 days (Exp. 1) or 14 days (Exp. 2, 3) and the lungs removed for examination. The tumor foci were counted with the help of a dissecting microscope. No overt signs of toxicity were seen in these mice after the i.p. administration of forskolin. FIG. 2 presents typical specimens of lungs from untreated and forskolin-treated mice of experiments 2 and 3. Examination under a dissecting microscope revealed that the tumor foci in the forskolin-treated mice were smaller and more superficial than in the untreated mice, which were larger and more deeply embedded. A summary of these experiments is provided in Table 1 below.

TABLE I

| | No. of pulmonary tumor foci* | Median number | p value |
|---|---|---|---|
| CONTROL MICE | | | |
| Experiment 1 ($2 \times 10^5$ cells/mouse) | 62,69,103,189, 191,281,350 | 189 | |
| FORSKOLIN-TREATED MICE | | | |
| | 0,17,31,32,47,89 | 3.1 | 0.014 |
| CONTROL MICE | | | |
| Experiment 2 ($3 \times 10^5$ cells/mouse) | 6,111,189,210,248, 267,276 | 210 | |
| FORSKOLIN-TREATED MICE | | | |
| | 0,0,1,1,48,115 | 1 | 0.004 |
| CONTROL MICE | | | |
| Experiment 3 ($3 \times 10^5$ cells/mouse) | >600 in each of nine mice** | >600 | |
| FORSKOLIN-TREATED MICE | | | |
| | 0,0,81,123,176, 219,250,281 | 149.5 | <0.001 |

*Each value is the no. of pulmonary foci per mouse.
**Estimated value. The lungs were fully occupied by tumor foci. (See FIG. 2c). In experiment 3, the mice were younger (about 5 weeks old).

EXAMPLE III

The in vitro experimental procedure of Example I above was repeated using a combination of forskolin and oxagrelate. In this example the cell suspension was added to platelet-rich plasma incubated with a mixture of forskolin and oxagrelate. It was found that low concentrations of oxagrelate (20 micromolar) and forskolin (0.4 micromolar) which were only slightly inhibitory alone (20 percent) acted synergistically (95 percent inhibition) when mixed with the platelets.

EXAMPLE IV

The in vivo experimental procedure of Example II above was also repeated using a combination of forskolin and oxagrelate. Intraperitoneal injections of the combination (oxagrelate: 40-45 mb/kg and forskolin: 1-1.5 mg/kg) 30 minutes before tail vein injections of the B16-F10 tumor cells reduced tumor colonization in the lungs of the mice 40 to 70 percent without treating the injected tumor cells per se.

What is claimed is:

1. A method for preventing metastatic disease in a human or animal suffering from a tumor without treating the primary tumor, the method comprising: administering a forskolin compound to said human or animal in amount effective to inhibit metastatic tumor cell-platelet interactions, the compound having the formula:

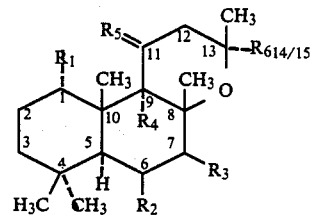

where $R_1$ is hydrogen or a hydroxy or lower alkoxy, sulfonate or carbonate group;
where $R_2$ is a hydroxy, carbonate, acetyl, or acetoxy or lower alkanoyl group;
where $R_3$ is a hydroxy, carbonate, acetyl or acetoxy or lower alkanoyl or tosyl group;
where $R_4$ is hydrogen or a hydroxy or lower alkoxy, sulfonate or carbonate group;
where $R_5$ is either double-bonded oxygen or separately bound hydrogen and hydroxy groups; and
where $R_6$ is a lower alkene or oxygen.

2. The method of claim 1 wherein the forskolin compound has the formula:

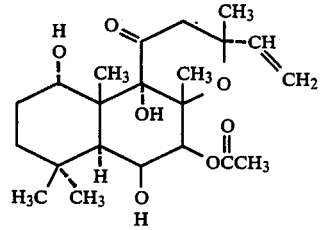

3. The method of claim 1 wherein the method further includes administering to said human or animal suffering from a tumor in conjunction with said forskolin compound a nucleoside transport inhibitor selected from the group consisting of p-nitrobenzylthionosine, dilazep, dipyridamole, oxagrelate and papaverine in an amount effective to retard adenosine uptake by red blood cells.

4. The method of claim 1 wherein the method further includes administering to said human or animal suffering from a tumor in conjunction with said forskolin compound a cAMP-blocking agent selected from the group consisting of theophylline, dipyridamole, oxagrelate and papaverine in an amount effective to block the action of cAMP phosphodiesterase in converting cAMP to AMP.

5. The method of claim 1 wherein the method further includes administering to said human or animal suffering from a tumor in conjunction with said forskolin compound as adenylate cyclase stimulating agent selected from the group consisting of prostaglandin E, $N^6$-phenyladenosine and 2-fluoroadenosine in an amount effective to stimulate membrane adenylate cyclase.

6. A pharmaceutical composition for preventing metastatic disease in a human or animal suffering from a tumor without treating the primary tumor, the composition comprising an effective amount of forskolin compound having the formula

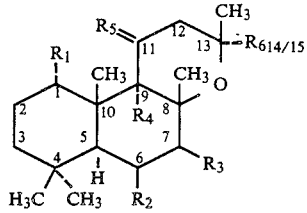

where $R_1$ is hydrogen or a hydroxy or lower alkoxy, sulfonate or carbonate group;

where $R_2$ is a hydroxy, carbonate, acetyl, or acetoxy or lower alkanoyl group;

where $R_3$ is a hydroxy, carbonate, acetyl or acetoxy or lower alkanoyl or tosyl group;

where $R_4$ is hydrogen or a hydroxy or lower alkoxy, carbonate or carbonate group;

where $R_5$ is either double-bonded oxygen or separately bound hydrogen and hydroxy groups; and where $R_6$ is a lower alkene or oxygen, and a nucleoside transport inhibitor selected from the group consisting of p-nitrobenzylthionosine, dilazep, dipyridamole, oxagrelate and papervine in an amount effective to retard adenosine uptake by red blood cells.

7. The composition of claim 6 wherein the forskolin compound has the following formula:

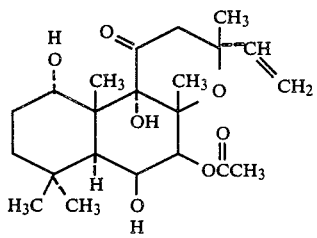

8. A pharmaceutical composition for preventing metastatic disease in a human or animal suffering from a tumor without treating the primary tumor the composition comprising an effective amount of a forskolin compound having the formula:

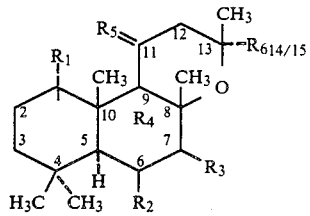

where $R_1$ is hydrogen or a hydroxy or lower alkoxy, sulfonate or carbonate group;

where $R_2$ is a hydroxy, carbonate, acetyl, or acetoxy or lower alkanoyl group;

where $R_3$ is a hydroxy, carbonate, acetyl or acetoxy or lower alkanoyl or tosyl group;

where $R_4$ is hydrogen or a hydroxy or lower alkoxy, sulfonate or carbonate group;

where $R_5$ is either double-bonded oxygen or separately bound hydrogen and hydroxy groups; and where $R_6$ is a lower alkene or oxygen, and a cAMP-blocking agent selected from the group consisting of theophylline, dipyridamole, oxagrelate and papaverine in an amount effective to block the action of cAMP phosphodiesterase in converting cAMP to AMP.

9. The composition of claim 8 wherein the cAMP-blocking agent is oxagrelate.

10. The composition of claim 8 wherein the forskolin compound has the following formula:

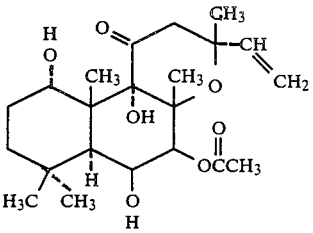

* * * * *